United States Patent
Moraitis

(10) Patent No.: US 11,073,523 B2
(45) Date of Patent: *Jul. 27, 2021

(54) METHOD FOR DIFFERENTIALLY DIAGNOSING ACTH-DEPENDENT CUSHING'S SYNDROME

(71) Applicant: Corcept Therapeutics, Inc., Menlo Park, CA (US)

(72) Inventor: Andreas G. Moraitis, Sunny Isles Beach, FL (US)

(73) Assignee: Corcept Therapeutics, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/690,423

(22) Filed: Nov. 21, 2019

(65) Prior Publication Data

US 2020/0088745 A1    Mar. 19, 2020

Related U.S. Application Data

(63) Continuation of application No. 15/987,365, filed on May 23, 2018, now Pat. No. 10,495,650, which is a continuation of application No. 15/796,443, filed on Oct. 27, 2017, now Pat. No. 10,006,924, which is a continuation of application No. 15/236,015, filed on Aug. 12, 2016, now Pat. No. 9,829,495.

(60) Provisional application No. 62/204,723, filed on Aug. 13, 2015.

(51) Int. Cl.
| | |
|---|---|
| *A61K 31/567* | (2006.01) |
| *A61K 31/4745* | (2006.01) |
| *A61K 31/573* | (2006.01) |
| *G01N 33/74* | (2006.01) |

(52) U.S. Cl.
CPC ......... *G01N 33/74* (2013.01); *A61K 31/4745* (2013.01); *A61K 31/567* (2013.01); *A61K 31/573* (2013.01); *G01N 2333/695* (2013.01); *G01N 2800/048* (2013.01)

(58) Field of Classification Search
CPC ............... A61K 31/573; A61K 31/567; A61K 31/4745; G01N 33/74
See application file for complete search history.

(56) References Cited

U.S. PATENT DOCUMENTS

| | | |
|---|---|---|
| 8,557,839 B2 | 10/2013 | Clark et al. |
| 8,598,149 B2 | 12/2013 | Belanoff |
| 8,921,348 B2 | 12/2014 | Belanoff |
| 9,829,495 B2 | 11/2017 | Moraitis |
| 10,006,924 B2 | 6/2018 | Moraitis |
| 2004/0138516 A1 | 7/2004 | Osorio et al. |
| 2014/0038926 A1 | 2/2014 | Hunt et al. |
| 2014/0162361 A1 | 6/2014 | Clark et al. |
| 2014/0170768 A1* | 6/2014 | Ehrenkranz ............ G01N 33/74 436/501 |
| 2016/0310507 A1* | 10/2016 | Belanoff .............. A61K 31/136 |
| 2017/0045535 A1 | 2/2017 | Moraitis |
| 2018/0052178 A1 | 2/2018 | Moraitis |

FOREIGN PATENT DOCUMENTS

| | | |
|---|---|---|
| WO | 2004041215 A2 | 5/2004 |
| WO | 2005070893 A2 | 8/2005 |
| WO | 2005087769 A1 | 9/2005 |
| WO | 2006014394 A1 | 2/2006 |
| WO | 2007131041 A2 | 11/2007 |
| WO | 2008060391 A2 | 5/2008 |
| WO | 2009050136 A2 | 4/2009 |
| WO | 2013177559 A2 | 11/2013 |
| WO | 2013190097 A1 | 12/2013 |

OTHER PUBLICATIONS

"Medical Encyclopedia of Medline", Available on Internet at: http://www.nimxih.govimedlinepluslencylartiele/003430.1itm, Oct. 2005, 4 pages.
Albertson et al., "Effect of the Antiglucocorticoid RU486 on Adrenal Steroidogenic Enzyme Activity and Steroidogenesis", Eur J Endocrinol., vol. 130, No. 2, Feb. 1994, pp. 195-200.
Asser et al., "Autocrine Positive Regulatory Feedback of Glucocorticoid Secretion: Glucocorticoid Receptor Directly Impacts H295R Human Adrenocortical Cell Function", Mol Cell Endocrinol., vol. 395, No. 1-2, Sep. 2014, pp. 1-9.
Beaufrere et al., "RU 486 Administration in a Child with Cushing's Syndrome", The Lancet, vol. 330, No. 8552, Jul. 25, 1987, 1 page.
Benagiano et al., "Selective Progesterone Receptor Modulators 3: Use in Oncology, Endocrinology and Psychiatry", Expert Opin. Pharmacother, vol. 9, No. 14, Oct. 2008, pp. 2487-2496.
Bertagna et al., "Pituitary-Adrenal Response to the Antiglucocorticoid Action of RU 486 in Cushing's Syndrome", J. Clin Endocrinol Metab, vol. 63, No. 3, Sep. 1986, pp. 639-643.
Chrousos et al., "Glucocorticoids and Glucocorticoid Antagonists: Lessions from RU 486", Kidney International, vol. 34, Suppl. 26, Oct. 1988, pp. S-18-S-23.
Chu et al., "Successful Long-Term Treatment of Refractory Cushing's Disease with High-Dose Mifepristone (RU 486)", J. Clin Endocrinology Metab, vol. 86, No. 8, Aug. 2001, pp. 3568-3573.

(Continued)

*Primary Examiner* — Dennis Heyer

(74) *Attorney, Agent, or Firm* — Kilpatrick Townsend & Stockton LLP

(57) ABSTRACT

This invention provides for an improved method for differentially diagnosing ACTH-dependent Cushing's syndrome. Current practice for differentially diagnosing ectopic ACTH syndrome and Cushing's Disease measures relative ACTH concentrations from the inferior petrosal venous sinus compared to fluid obtained from a periphery venous sample. This is performed before and after administration of exogenous corticotropin releasing factor, or after administration of metyrapone. This invention uses glucocorticoid receptor antagonists to induce release of endogenous CRH which stimulates ACTH to increase in patients with ectopic ACTH syndrome but not in those with Cushing's Disease.

20 Claims, No Drawings

(56) References Cited

OTHER PUBLICATIONS

Cuneo et al., "Metyrapone Pre-Treated Inferior Petrosal Sinus Sampling in the Differential Diagnosis of ACTH-Dependent Cushing's Syndrome", Clinical Endocrinolog, vol. 46, No. 5, May 1997, pp. 607-618.
Ehrenkranz et al., "SUN-66: Using Mifepristone to Differentiate Cushing's Disease from Cushing's Syndrome", The Endocrine Society's 95th Annual Meeting and Expo, Jun. 15-18, 2013, 2 pages.
El-Shafie et al., "Adrenocorticotropic Hormone-Dependent Cushing's Syndrome: Use of an Octreotide Trial to Distinguish between Pituitary or Ectopic Sources", Sultan Qaboos University Medical Journal, vol. 15, Issue 1, Jan. 2015, pp. 120-123.
EP16836011.3, "Extended European Search Report", dated Dec. 17, 2018, 9 pages.
Fleseriu et al., "Changes in Plasma ACTH Levels and Corticotroph Tumor Size in Patients With Cushing's Disease During Long-term Treatment with the Glucocorticoid Receptor Antagonist Mifepristone", J. Clin. Endocrinol. Metab., vol. 99, No. 10, Oct. 2014, pp. 3718-3727.
Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Jun. 2012, pp. 2039-2049.
Gross et al., "Mifepristone Reduces Weight Gain and Improves Metabolic Abnormalities Associated With Risperidone Treatment in Normal Men", Obesity (Silver Spring), vol. 18, No. 12, Dec. 2010, pp. 2295-2300.
Healy et al., "Pituitary and Adrenal Responses to the Antiprogesterone and Anti-glucocorticoid Steroid RU486 in Primates", Journal of Clinical Endocrinology & Metabolism, vol. 57, No. 4, Nov. 1983, pp. 863-865.
Kawai et al., "Pharmacokinetic Properties of the Antiglucocorticoid and Antiprogesterone Steroid RU 486 in Man", The Journal of Pharmacology and Experimental Therapeutics, vol. 241, No. 2, May 1987, pp. 401-406.
Lee et al., "A Measure Of 1-15 Glucocorticoid Load Provided By Dna Methylation Ofin Mice", Psychopharmacology, vol. 218, No. 1, Apr. 21, 2011, pp. 302-312.
Lee et al., "Office of Clinical Pharmacology Review", NDA 20687 (Addendum, Korlym™, Mifepristone), 2012, pp. 1-119.
Lely et al., "Rapid Reversal of Acute Psychosis in the Cushing Syndrome with the Cortisol-Receptor Antagonist Mifepristone (RU 486)", Annals of Internal Medicine, vol. 114, No. 2, Jan. 15, 1991, pp. 143-144.
PCT/EP2008/063699, "International Search Report", dated May 6, 2009, 5 pages.
PCT/US2016/046904, "International Search Report and Written Opinion", dated Oct. 31, 2016, 7 pages.
PCT/US2017/013974, "International Search Report and Written Opinion", dated Apr. 20, 2017, 12 pages.
Reimondo et al., "The Corticotrophin-Releasing Hormone Test is the Most Reliable Noninvasive Method to Differentiate Pituitary from Ectopic ACTH Secretion in Cushing's Syndrome", Clinical Endocrinolog, vol. 58, No. 6, Jun. 2003, pp. 718-724.
Ritzel et al., "ACTH after 15 min Distinguishes Between Cushing's Disease and Ectopic Cushing's Syndrome: A Proposal for a Short and Simple CRH Test", Europe an Journal of Endocrinology, vol. 173, No. 2, Aug. 2015, pp. 197-204.
Sarkar, "Mifepristone: Bioavailability, Pharmacokinetics and Use-Effectiveness", European Journal of Obstetrics and Gynecology and Reproductive Biology, vol. 101, No. 2, Mar. 10, 2002, pp. 113-120.
Sartor et al., "Mifepristone: Treatment of Cushing's Syndrome", Clinical Obstetrics Gynecol, vol. 39, No. 2, Jun. 1996, pp. 506-510.
Sharma et al., "Prolactin as a Marker of Successful Catheterization during IPSS in Patients with ACTH-Dependent Cushing's Syndrome", The Journal of Clinical Endocrinology & Metabolism, vol. 96, Issue 12, Dec. 1, 2011, pp. 3687-3694.
Tsigos et al., "Differential Diagnosis and Management of Cushing's Syndrome", Annual Review of Medicine, vol. 47, Feb. 1, 1996, pp. 443-461.
Verhelst et al., "Short and Long-term Responses to Metyrapone in the Medical Management of 91 Patients with Cushing's Syndrome", Clinical Endocrinology, vol. 35, No. 2, Aug. 1991, pp. 169-178.
*Corcept Therapeutics, Inc.* v. *Teva Pharmaceuticals USA, Inc.*, Civil Action No. 2:18-cv-03632, In the US District Court for the District of New Jersey, "Expert Report of Dr. Richard Pestell, M.D., Concerning the Invalidity of U.S. Pat. Nos. 8,921,348 and 9,829,495," (Nov. 2, 2020), pp. 1-220.
Castinetti, et al., "Merits and pitfalls of mifepristone in Cushing's syndrome," Eur. J. Endocrinol. 160:1003-1010 (2009) (TEVA_MIFE-0071132-139).
Colao, et al., Inferior petrosal sinus sampling in the differential diagnosis of Cushing's syndrome: results of an Italian multicenter study, European Journal of Endocrinology (2001) 144:499-507 (TEVA_MIFE-0071132-0071159-167).
Corrigan, et al., "Selective Venous Sampling to Differentiate Ectopic Secretion from Pituitary Cushing's Syndrome," The New England Journal of Medicine, Apr. 14, 1977, 296(15):861-862 (TEVA_MIFE-0071168--170).
Findling, et al., "Selective Venous Sampling for ACTH in Cushing's Syndrom; Differentiation Between Cushing's Disease and the Ectopic ACTH Syndrome," Annals of Internal Medicine (May 1981), 94(5):647-652 (TEVA_MIFE-0071340-346).
Findling, et al., "Routine Inferior Petrosal Sinus Sampling in the Differential Diagnosis of Adrenocorticotropin (ACTH)-Dependent Cushing's Syndrome: Early Recognition of the Occult Ectopic ACTH Syndrome," Journal of Clinical Endocrinology and Metabolism, (1991) 73(2):408-413 (TEVA_MIFE-0071347-354).
Johanssen, et al., "Mifepristone (RU 486) in Cushing's Syndrome," European J. Endocrin. 157:561-69 (2007) (TEVA_MIFE-0071535-545).
Kaltsas, et al., "A Critical Analysis of the Value of Simultaneous Inferior Petrosal Sinus Sampling in Cushing's Disease and the Occult Ectopic Adrenocorticotropin Syndrome," The Journal of Clinical Endocrinology & Metabolism, (Feb. 1999) 84(2):487-492 (TEVA_MIFE-0071546-552).
Nieman, et al., "Successful Treatment of Cushing's Syndrome with the Glucocorticoid Antagonist RU 486*," J Clin. Endocrinol. Metab. 61(3): 536-540 (1985) (TEVA_MIFE-0071808-813).
Oldfield, et al., "Petrosal Sinus Sampling with and without Corticotropin-Releasing Hormone for the Differential Diagnosis of Cushing's Syndrome," The New England Journal of Medicine, (Sep. 26, 1991), 325(13):897-905 (TEVA_MIFE-0121427-435).
Oliver, et al., "Characterisation of ACTH Related Peptides in Ectopic Cushing's Syndrome," Pituitary, (2003), 6:119-126, (TEVA_MIFE-0121436-443).
Sartor, et al., "Mifepristone: Treatment of Cushing's Syndrome," Clinical Obstetrics and Gynecology 39(2): 506-510 (1996) (TEVA_MIFE-0071975-979).
Tabarin, et al., "Usefulness of the Corticotropin-Releasing Hormone Test during Bilateral Inferior Petrosal Sinus Sampling for the Diagnosis of Cushing's Disease," Journal of Clinical Endocrinology and Metabolism, (1991), 73(1):53-59 (TEVA_MIFE-0072030-038).
Utz, et al., "The Role of Bilateral Inferior Petrosal Sinus Sampling in the Diagnosis of Cushing's Syndrome," Arq Bras Endocrinol Metab, (2007), 51(8):1329-1338 (TEVA_MIFE-0072090-099).
Gutiérrez-Restrepo et al., "Cushing's Syndrome", Laboratory Medicine, vol. 15, Nos. 9-10, 2009, 20 pages.

\* cited by examiner

METHOD FOR DIFFERENTIALLY DIAGNOSING ACTH-DEPENDENT CUSHING'S SYNDROME

CROSS-REFERENCES TO RELATED APPLICATIONS

This application is a continuation of, and claims priority under 35 U.S.C. § 120 to, U.S. patent application Ser. No. 15/987,365, filed May 23, 2018, which is a continuation of Ser. No. 15/796,443, filed Oct. 27, 2017 (now U.S. Pat. No. 10,006,924, issued Jun. 26, 2018), which is a continuation of U.S. patent application Ser. No. 15/236,015, filed Aug. 12, 2016, (now U.S. Pat. No. 9,829,495, issued Nov. 28, 2017), which application claims the benefit under 35 U.S.C. § 119(e) of U.S. Provisional Patent Application Ser. No. 62/204,723, filed Aug. 13, 2015, the entire contents of which applications are hereby incorporated by reference in their entireties.

BACKGROUND OF THE INVENTION

Cortisol is a steroid produced by the adrenal glands and is used in the body to respond to physical and emotional stress and to maintain adequate energy supply and blood sugar levels. Cortisol production is highly regulated by the hypothalamic-pituitary-adrenal axis (HPA) through a complex set of direct influences and negative feedback interactions. In healthy individuals, insufficient cortisol in the bloodstream triggers the hypothalamus to release corticotropin-releasing hormone (CRH) which signals to the pituitary gland to release adrenocorticotropic hormone (ACTH), which in turn stimulates the adrenal glands to produce more cortisol. Excessive cortisol inhibits hypothalamus from producing CRH, thus inhibiting the pituitary gland from releasing ACTH, which in turn suppresses cortisol production. The HPA regulation also results in a diurnal rhythm of cortisol levels, reaching peaks in the morning and nadirs around midnight. Pathological conditions associated with the HPA can affect the diurnal rhythm of the cortisol and ACTH production and cause serious health problems.

Cushing's syndrome is one of these problems. Patients having Cushing's syndrome usually have easy bruising; abdominal obesity and thin arms and legs; facial plethora; acne; proximal muscle weakness; and/or red purple stripes across the body. Cushing's syndrome is accompanied by hypercortisolemia, a condition involving a prolonged excess of circulating cortisol. Cushing's syndrome can be classified as exogenous Cushing's syndrome, which is caused by excess use of glucocorticoids drugs, such as prednisone, dexamethasone, and hydrocortisone, and endogenous Cushing's syndrome, which is caused by deregulatory abnormalities in the HPA axis. Endogenous Cushing's syndrome consists of the ACTH-independent Cushing's syndrome, characterized by an overproduction of cortisol in the absence of elevation of ACTH secretion; the ACTH-dependent Cushing's syndrome, characterized by excessive ACTH secretion.

ACTH-dependent Cushing's syndrome includes roughly 80% of patients having endogenous Cushing's syndrome and consists of two major forms: Cushing Disease and ectopic ACTH syndrome. The former is caused by a pituitary tumor and the latter is caused by a tumor outside the pituitary. Correct differential diagnosis between the Cushing Disease and ectopic ACTH syndrome is important for endocrinologists to recommend transphenoidal surgery or appropriate imaging to identify source of the ectopic ACTH secretion.

One current approach of differentially diagnosing patients with ACTH-dependent Cushing's syndrome involves measuring ACTH levels from samples obtained simultaneously from both inferior petrosal venous sinus (IPS)—a procedure referred to as inferior petrosal venous sinus sampling (IPSS)—and from the internal jugular or another peripheral vein. In one approach, referred herein as CRH-IPSS, 5 blood samples are taken from each IPS and the internal jugular vein, two before and three after administration of CRH. A central-to-periphery ACTH ratio of >2 before and >3 after the administration of CRH is consistent with Cushing Disease while a lower ratio favors ectopic ACTH syndrome. This procedure requires prolonged catheterization with the likelihood of infection, thrombosis, or bleeding rising with the duration of catheterization. In addition CRH is a protein which is expensive to produce, causing a shortage in supply between 2011 and early 2013, and requires sophisticated handling. Thus, the results from CRH-IPSS for differentially diagnosing patients with ACTH-dependent Cushing's syndrome often fall in the gray area. Desmopressin acetate (DDAVP), the alternative to CRH, which has also been used for IPSS, has similar disadvantages.

Another approach, referred herein as metyrapone-IPSS, is similar to the one above, except that metyrapone instead of CRH is administered to the patient before IPSS and that samples are only taken from the patients after the metyrapone administration. Although metyrapone-IPSS improves the CRH-IPSS—since it dispenses with the need for sampling before the administration of metyrapone, and thus reduces the duration of catheterization and likelihood of infection, thrombis, or bleeding associated therewith—it also has serious limitations. First, metyrapone acts to block the conversion of 11-deoxycortisol to cortisol by 11β-hydroxylase, causing a decrease in cortisol level, which in turn stimulates ACTH production and release. Since its effect on the ACTH secretion is indirect, the test result may be skewed by other factors affecting the cortisol synthesis. Second, as a cortisol synthesis blocker, treatment of metyrapone—especially at a high dose—may result in adrenal insufficiency or have deleterious effects on various normal bodily functions that require cortisol—for example, the anti-stress and anti-inflammation functions. Third, metyrapone is currently not available in the United States, consequently this diagnosis method is out of reach for many patients in this country.

BRIEF SUMMARY OF THE INVENTION

In a first aspect, provided herein is a method of differentially diagnosing adrenocorticotropic hormone (ACTH)-dependent Cushing's syndrome in a patient with hypercortisolemia where the differential diagnosis is between ectopic ACTH syndrome and Cushing Disease. The method comprises: (i) selecting a patient with Cushing's syndrome and elevated ACTH levels; (ii) administering a dose of glucocorticoid receptor antagonist (GRA) sufficient to increase ACTH from the pituitary gland by at least two fold in persons with normal HPA function; (iii) waiting for at least two hours; and (iv) obtaining from the patient an ACTH concentration ratio, which is derived both from the ACTH concentrations in fluid obtained from either the left or right inferior petrosal venous sinus and from fluid obtained from a periphery vein, e.g., a jugular vein. The patient is diagnosed with Cushing Disease if the ACTH concentration ratio is greater than 3.

In some embodiments, the periphery venous sample is a jugular venous sample. In some embodiments, the ratio is derived from the ACTH concentration in fluid obtained from the left and right inferior petrosal venous sinuses. In some embodiments, the GRA is a selective inhibitor of the glucocorticoid receptor. In some cases, the first and second samplings of ACTH are taken 5-10 minutes apart from both the inferior petrosal venous sinus and a periphery venous sample.

In some cases, the GRA is a selective inhibitor of the glucocorticoid receptor. In some embodiments, the GRA comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the GRA is mifepristone. In some embodiments, the GRA is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9(11)-dien-3-one. In some embodiments, the glucocorticoid receptor antagonist is (11β,17β)-11-(1,3-benzodioxol-5-yl)-17-hydroxy-17-(1-propynyl)estra-4,9-dien-3-one.

In some embodiments, the GRA has a non-steroidal backbone. In some cases, the GRA backbone is a cyclohexyl pyrimidine. In some cases, wherein the cyclohexyl pyrimidine has the following formula:

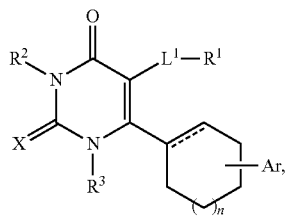

the dashed line is absent or a bond; X is selected from the group consisting of O and S; $R^1$ is selected from the group consisting of cycloalkyl, heterocycloalkyl, aryl, and heteroaryl, optionally substituted with 1-3 $R^{1a}$ groups; each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$, $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl, and heteroaryl; $R^{1b}$ and $R^{1c}$ are each independently selected from the group consisting of H and $C_{1-6}$ alkyl; $R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl; $R^3$ is selected from the group consisting of H and $C_{1-6}$ alkyl; Ar is aryl, optionally substituted with 1-4 $R^4$ groups; each $R^4$ is independently selected from the group consisting of H, $C_{1-6}$ alkyl, $C_{1-6}$ alkoxy, halogen, $C_{1-6}$ haloalkyl, and $C_{1-6}$ haloalkoxy; $L^1$ is a bond or $C_{1-6}$ alkylene; and subscript n is an integer from 0 to 3, or salts and isomers thereof.

In some cases, the GRA backbone is a fused azadecalin. In some cases, the fused azadecalin is a compound having the following formula:

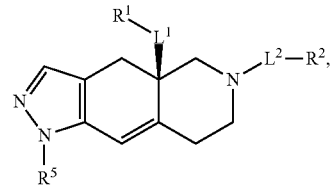

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$, and —$C(O)OR^{1A}$, wherein $R^{1A}$ is a member selected from hydrogen, unsubstituted alkyl, and unsubstituted heteroalkyl; $R^{1c}$ and $R^{1D}$ are members independently selected from unsubstituted alkyl and unsubstituted heteroalkyl, and are optionally joined to form an unsubstituted ring with the nitrogen to which they are attached, wherein said ring optionally comprises an additional ring nitrogen. $R^2$ has the formula:

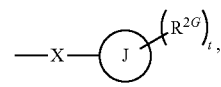

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, and $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the GRA backbone is a heteroaryl ketone fused azadecalin or an octahydro fused azadecalin. In some cases, the heteroaryl ketone fused azadecalin has the formula:

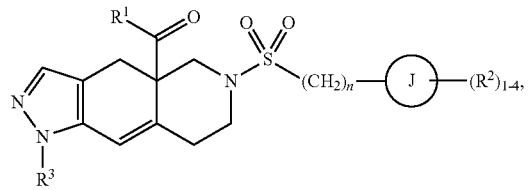

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring, and a heteroaryl ring, wherein the heterocycloalkyl and heteroaryl rings have from 5 to 6 ring members and from 1 to 4 heteroatoms each independently selected from the group consisting of N, O, and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O, and S, wherein the heterocycloalkyl ring is optionally substituted with 1-3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the octahydro fused azadecalin has the formula:

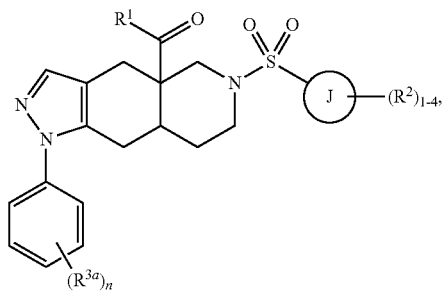

wherein $R^1$ is a heteroaryl ring having from 5 to 6 ring members and from 1 to 4 heteroatoms each independently selected from the group consisting of N, O, and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O, and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O, and S; alternatively, the two $R^2$ groups on adjacent ring atoms are combined to form a heterocycloalkyl ring having from 5 to 6 ring members and from 1 to 3 heteroatoms each independently selected from the group consisting of N, O, and S, wherein the heterocycloalkyl ring is optionally substituted with 1-3 $R^{2c}$ groups; $R^{2a}$, $R^{2b}$, and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In yet another aspect, provided herein is a diagnostic composition, or a diagnostic kit comprising a glucocorticoid receptor antagonist (GRA) for use in a method of differentially diagnosing adrenocorticotropic hormone (ACTH)-dependent Cushing's syndrome in a patient where the differential diagnosis is between ectopic ACTH syndrome and Cushing Disease, the method comprising the step of determining the ACTH concentration ratio from a patient with Cushing's syndrome and an elevated ACTH level, where the patient has been administered a dose of glucocorticoid receptor antagonist (GRA) at least two hours prior to the removal of venous samples and where the amount of GRA administered to the patient is sufficient to increase ACTH from the pituitary gland by at least two fold in persons with normal Hypothalmus Pituitary Adrenal (HPA) function; wherein the ACTH concentration ratio is derived from the ACTH concentrations in fluid obtained from either the left or right inferior petrosal venous sinus and from fluid obtained from a periphery venous sample; and wherein an ACTH concentration ratio of greater than 3 for the ACTH concentration from the inferior venous sinus sample over the periphery venous sinus sample is diagnostic indicative of Cushing's disease. In addition, all the embodiments in the first aspect described above are also included in this aspect of the disclosure.

In yet another aspect, provided here in is a method of obtaining a measurement indicative of differential diagnosis of adrenocorticotropic hormone (ACTH)-dependent Cushing's syndrome in a patient where the differential diagnosis is between ectopic ACTH syndrome and Cushing Disease, the method comprising the step of: (i) determining the ACTH concentration ratio from a patient with Cushing's syndrome and an elevated ACTH level, where the patient has been administered a dose of glucocorticoid receptor antagonist (GRA) at least two hours prior to the removal of venous samples and where the amount of GRA administered to the patient is sufficient to increase ACTH from the pituitary gland by at least two fold in persons with norma Hypothalmus Pituitary Adrenal (HPA) function; wherein the ACTH concentration ratio is derived from the ACTH concentrations in fluid obtained from either the left or right inferior petrosal venous sinus and from fluid obtained from a periphery venous sample; and wherein an ACTH concentration ratio of greater than 3 for the ACTH concentration from the inferior venous sinus sample over the periphery venous sinus sample is indicative of Cushing's disease. In addition, all the embodiments in the first aspect described above are also included in this aspect of the disclosure.

In yet another aspect, provided herein is a glucocorticoid receptor antagonist (GRA) for use in a method of differentially diagnosing adrenocorticotropic hormone (ACTH)-dependent Cushing's syndrome in a patient where the differential diagnosis is between ectopic ACTH syndrome and Cushing Disease, the method comprising the steps of: (i) selecting a patient with Cushing's syndrome and also elevated ACTH levels; (ii) administering a dose of the GRA sufficient to increase ACTH from the pituitary gland by at least two fold in persons with normal Hypothalmus Pituitary Adrenal (HPA) function; (iii) waiting for at least two hours; and (iv) obtaining from the patient an ACTH concentration ratio wherein the ratio is derived from the ACTH concentrations in fluid obtained from either the left or right inferior petrosal venous sinus and from fluid obtained from a periphery venous sample; wherein an ACTH concentration ratio of greater than 3 for the ACTH concentration from the inferior venous sinus sample over the periphery venous sinus sample is diagnostic of Cushing's disease. In addition, all the embodiments in the first aspect described above are also included in this aspect of the disclosure.

Other objects, features, and advantages of the present invention will be apparent to one of skill in the art from the following detailed description and FIGURES.

DETAILED DESCRIPTION OF THE INVENTION

I. Introduction

This invention involves the use of GRAs to provide a robust and reproducible means to stimulate ACTH production in the pituitary gland for the differential diagnosis of patients with ACTH-dependent Cushing's syndrome, where the differential diagnosis is between ectopic ACTH syndrome and Cushing Disease. GRAs are first administered, and blood samples are then taken by IPSS after sufficient time for the assessment of ACTH levels.

The claimed methods have many advantages over the existing differential diagnosis methods, such as CRH-IPSS, DDAVP-IPSS and metyrapone-IPSS. First, the claimed methods are more robust compared to metyrapone-IPSS. GRAs used in the invention act to block cortisol binding to the receptor—thus preventing cortisol from inhibiting ACTH production and resulting in increased ACTH production/secretion. Compared to metyrapone, which acts to block the cortisol synthesis pathway, GRAs' effect on ACTH stimulation is more direct, thus making the test results more reliable. Second, compared to CRH/DDAVP-IPSS, the methods are cost-effective and convenient to use because GRAs are orally deliverable and less expensive than CRH to manufacture and store. Third, compared to CRH/DDAVP-IPSS, the method disclosed herein dispenses with the need to sample blood before the administration of GRAs, and thus reduces the duration of catheterization and minimizes complications associated with prolonged catheterization.

II. Definitions

The term "endogenous Cushing's syndrome" refers to a form of Cushing's syndrome, where the excess cortisol level is caused by the body's own overproduction of cortisol.

The term "Adrenocorticotropic hormone (ACTH)-dependent Cushings syndrome" refers to a form of endogenous Cushing's syndrome, which is caused by abnormal production of ACTH. There are two major forms of ACTH-dependent Cushing's syndrome: Cushing Disease (accounting for about 80% of the cases) and ectopic ACTH syndrome (accounting for 20% of the cases).

The term "ACTH concentration ratio", "ACTH ratio", "pituitary to periphery ACTH ratio", or "central to periphery ACTH ratio" disclosed herein refers to the ratio between the amount, level, or concentration of ACTH in the blood sample obtained from inferior petrosal sinus and the blood sample obtained from the periphery veins. In one embodiment, the periphery vein is the jugular vein.

The term "prolactin concentration ratio", "prolactin ratio", "pituitary to periphery prolactin ratio", or "central to periphery prolactin ratio" disclosed herein refers to the ratio between the amount, level, or concentration of prolactin in the blood sample obtained from inferior petrosal sinus and the blood sample obtained from the periphery veins. In one embodiment, the periphery vein is the jugular vein.

The term "differentially diagnosing" refers to the distinguishing of a particular disease or condition from others that present similar symptoms. A differential diagnostic method is a systematic diagnostic method used to identify the presence of a condition where multiple alternatives are possible. This method is essentially a process of elimination or a process of obtaining information that shrinks the "probabilities" of candidate conditions to negligible levels. The method uses evidence such as symptoms, test results, patient history, and medical knowledge to adjust epistemic confidences in the mind of the diagnostician (or, for computerized or computer-assisted diagnosis, the software of the system). Often each individual option of a possible disease is called a differential diagnosis.

The term "ectopic ACTH syndrome" refers to the abnormal production of ACTH due to ectopic ACTH secretion by an extrapituitary tumor. These extrapituitary tumors frequently originate in lungs, but in some cases originate from the thymus, pancreas, adrenal gland or thyroid.

The term "Cushing Disease" refers to the condition in which the pituitary gland releases too much ACTH as a result of a tumor located in—or excess growth (hyperplasia) of—the pituitary gland. Cushing Disease is a form of Cushing's syndrome.

The term "hypercortisolemia" refers a condition of having a higher than normal amount of circulating cortisol.

The term "inferior petrosal sinus sampling (IPSS)" refers to an invasive procedure performed to obtain blood samples from one or both petrosal venous sinuses by inserting catheters in one or both inferior petrosal veins via the jugular or femoral veins. The petrosal venous sinus drains the pituitary via the cavernous sinus. Thus, samples obtained from IPSS are often analyzed and compared with the samples obtained from periphery blood for the amount of a particular analyte to detect signs of a disease relating to the pituitary gland.

The term "jugular venous sampling" refers to an invasive procedure performed to obtain blood samples from jugular veins (a periphery vein) by inserting catheters in the internal jugular vein via femoral veins. The tips of the catheters are typically advanced to the level of the angles of the mandible.

The term "periphery venous sinus sampling" refers to an invasive procedure performed to obtain blood samples from periphery veins by catheterization. Non-limiting examples of periphery veins include adrenal veins, high inferior vena cava, hepatic vein, azygos and hemiazygos veins, right atrium, right and left innominate and thymic veins, jugular veins, and both superior and middle thyroid veins.

The term "patient," "individual", or "subject" is used interchangeably to refer to a human subject. In some cases, the individual is suspected of having adrenal insufficiency.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, and transdermal patches.

The term "sample" refers to a biological sample obtained from a human subject. The sample can be any cell, tissue or fluid from a human subject. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification.

The term "cortisol" refers to a glucocorticoid hormone that is produced by the zona fasciculata of the adrenal gland.

The term "adrenocorticotropic hormone" or "ACTH" refers to a polypeptide-based hormone that is normally produced and secreted by the anterior pituitary gland.

ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids.

The term "measuring the level," in the context of cortisol, ACTH, or other steroids, refers determining, detecting, or quantitating the amount, level, or concentration of, for example, cortisol, ACTH or other steroids in a sample obtained from a subject.

The term a "increase" or a "decrease" refers to a detectable positive or negative change in quantity from a comparison control, e.g., an established standard control (such as an average level of cortisol in a normal, healthy subject who does not have hypercortisolemia). An increase is a positive change that is typically at least 5%, at least 10%, or at least 20%, or 50%, or 100%, and can be as high as at least 1.5-fold, at least 2-fold, at least 5-fold, or even 10-fold of the control value. Similarly, a decrease is a negative change that is typically at least 5%, at least 10%, or at least 20%, 30%, or 50%, or even as high as at least 80% or 90% of the control value. Other terms indicating quantitative changes or differences from a comparative basis, such as "more," "less," 'higher," and "lower," are used in this application in the same fashion as described above.

The term "normal reference value", "reference value", or "standard control level" refers to the a predetermined amount, level, or concentration of a particular analyte, e.g., ACTH, cortisol, or prolactin—by comparison to which a diagnosis of the presence or absence of a particular condition can be made, e.g., hypercortisolemia. Normal reference values referred to in this disclosure are in some cases provided by the commercial test that is used to determine the analyte levels. In some cases, a normal reference value, reference value, or standard control level is established as the average of the amount, level, or concentration of an analyte from one or more normal, healthy subjects, e.g., subjects who have normal HPA function. In some cases, they are established as a range of the level, amount, or concentration of the analyte in a group of healthy subjects. Normal reference values may vary depending on the nature of the sample, the manner or timing of sample collection, as well as other factors such as the sex, age, and ethnicity of the subjects for whom such a control value is established.

The term "elevated level", "elevated amount", or "elevated concentration" refers to the level or amount of the analyte that is higher than the normal reference value for that analyte.

The term "chromatography" refers to a process in which a chemical mixture carried by a liquid or gas is separated into components as a result of the differential distribution of the chemical entities as they flow around or over a stationary liquid or solid phase.

The term "liquid chromatography" or "LC" refers to a process of selective retardation of one or more components of a fluid solution when the fluid uniformly percolates either through a column of a finely divided substance or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

The term "high performance liquid chromatography" or "HPLC" (also sometimes known as "high pressure liquid chromatography") refers to liquid chromatography in which the degree of separation is increased by forcing the mobile phase under pressure through a stationary phase—typically a densely packed column. As used herein, the term "ultra high performance liquid chromatography", "HPLC" or "UHPLC" (sometimes known as "ultra high pressure liquid chromatography") refers to HPLC which occurs at much higher pressures than in traditional HPLC techniques.

The term "glucocorticosteroid" ("GC") or "glucocorticoid" refers to a steroid hormone that binds to a glucocorticoid receptor. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

The term "glucocorticoid receptor" ("GR") refers to the type II GR which specifically binds to cortisol and/or cortisol analogs such as dexamethasone; See, e.g., Turner & Muller, *J Mol. Endocrinol,* 2005 (35): 283-292. The GR is also referred to as the cortisol receptor. The term includes isoforms of GR, recombinant GR and mutated GR. Inhibition constants ($K_i$) against the human GR receptor type II (Genbank: P04150) are between 0.0001 nM and 1,000 nM; preferably between 0.0005 nM and 10 nM, and most preferably between 0.001 nM and 1 nM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than to other nuclear receptors, such as the mineralocorticoid receptor (MR), androgen receptor (AR), or progesterone receptor (PR). It is preferred that the specific glucocorticoid receptor antagonist binds GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds a GR with an affinity that is 100× greater ($1/100^{th}$ the $K_d$ value) than its affinity to the MR, AR, or PR, both the MR and PR, both the MR and AR, both the AR and PR, or to the MR, AR, and PR.

The term "selective inhibitor" in the context of a glucocorticoid receptor refers to a chemical compound that selectively interferes with the binding of a specific glucocorticoid receptor agonist and a glucocorticoid receptor.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

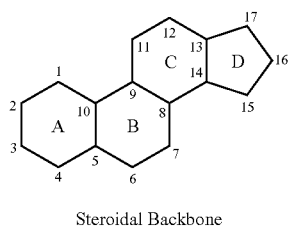

Formula I

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the term "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic, and non-peptidic molecular entities.

Non-steroidal GRA compounds also include glucocorticoid receptor antagonists having a cyclohexyl-pyrimidine backbone, a fused azadecalin backbone, a heteroaryl ketone fused azadecalin backbone, or an octahydro fused azadecalin backbone. Exemplary glucocorticoid receptor antagonists having a cyclohexyl-pyrimidine backbone include those described in U.S. Pat. No. 8,685,973. Exemplary GRAs having a fused azadecalin backbone include those described in U.S. Pat. Nos. 7,928,237 and 8,461,172. Exemplary GRAs having a heteroaryl ketone fused azadecalin backbone include those described in U.S. Pat. Pub. 2014/0038926. Exemplary GRAs having an octohydro fused azadecalin backbone include those described in U.S. Provisional Patent Appl. No. 61/908,333, entitled Octahydro Fused Azadecalin Glucocorticoid Receptor Modulators, filed on Nov. 25, 2013.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_1$-6. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —S(O)$_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

III. Detailed Descriptions of Embodiments

A. Method For Differential Diagnosis of ACTH-Dependent Cushing's Syndrome

1. Selecting Patients Having ACTH-Dependent Cushing's Syndrome

The methods disclosed herein is used to provide differential diagnosis between Cushing Disease and ectopic ACTH syndrome to patients who have already been diagnosed as having ACTH-dependent Cushing's syndrome. A diagnosis of ACTH-dependent Cushing's syndrome can be made based on observation of certain clinical symptoms, the detection of hypercortisolemia and elevated blood ACTH levels.

a. Clinical Symptoms

Eligible patients may exhibit one or more of the following symptoms: easy bruising; abdominal obesity and thin arms and legs; facial plethora; acne; proximal myopathy (or proximal muscle weakness); striae (especially if reddish purple and 1 cm wide); and thin skin. Patients may also frequently feel changes in mood; change in appetite, headaches; a chronic feeling of tiredness; osteoporosis; low potassium; diabetes, and high blood pressure; decreased concentration peripheral edema hypokalemia; decreased libido acne kidney stones; impaired memory (especially short term); and unusual infections. Females patients may have irregular menstruation, hirsutism, or female balding. Pediatric patients may have weight gain with decreasing growth velocity; abnormal genital virilization; short stature; and pseudoprecocious puberty or delayed puberty. The next step is to confirm these patients have hypercortisolemia.

b Hypercortisolemia

A diagnosis of hypercortisolemia requires the determination of the patient's circulating cortisol level. Various types of samples that can be used for this purpose, such as saliva, urine, whole blood, serum, and plasma. Samples may also be collected at different time during the day. In one approach, the patient's whole blood sample is collected and processed to collect serum, i.e., in the morning, e.g., at 8 am. or in the afternoon, e.g., at 4 pm. The collected serum sample is refrigerated or frozen within, e.g., 2 hours of collection. Analysis of the serum sample is performed in a timely fashion, e.g. within 7 days from sample collection. In another approach, the patient's cortisol levels are measured from his or her saliva samples. Salivary cortisol is in equilibrium with the free cortisol in blood circulation. Changes of cortisol levels in the bloodstream are paralleled, within minutes, by similar alterations in salivary cortisol concentrations, such that one can use the latter as a surrogate of the former. The commonly used saliva-based cortisol test is the midnight saliva test, which measures cortisol levels from saliva samples collected at between 11 pm and midnight. Intake of food or drink is prohibited at least 15 minutes prior to sample collection. Saliva samples are collected by keeping and rolling a swab in mouth for approximately 2 minutes. The saliva samples, ambient or refrigerated, are then sent to a laboratory for cortisol level determination in a timely fashion, e.g., within 7 days from sample collection.

Methods for measuring cortisol levels are known to those in the art. Useful assays include immunoassays, e.g., competitive immunoassay, radioimmunoassay, immunofluorometric enzyme assay, and ELISA, competitive protein-binding assay and mass spectrometry, e.g., high-performance liquid chromatography/triple quadrupole-mass spectrometry (LC-MS/MS). Commercial kits for measuring cortisol in samples are available from Beckman-Coulter, Seimens, Roche Diagnostics, and the like. Non-limiting examples of cortisol tests are Mayo Clinic's SALCT, CORT, CORTU, and CINP tests; an ADVIA Centaur® Cortisol assay (Siemens Healthcare Global); ARCHITECT i2000SR cortisol (Abbott); Immulite® 2000 Cortisol assay (Siemans Healthcare Global; #L2KCO2), Vitros® ECi Cortisol assay (Ortho Clinical Diagnostics; #107 4053), and Elecsys® Cortisol Immunoassay (Roche Molecular Diagnostics; #11875116160).

The patient's cortisol measurement is then compared with the normal reference value; a level higher than the normal reference value indicates the patient has hypercortisolemia. The normal reference values for cortisol levels vary depending on the nature of the samples, the manner and timing of sample collection (higher for samples collected in the morning and lower for samples collected at night), and the detection method. Thus, it is essential to interpret test results in the context of the appropriate normal reference values. Various commercial kits provide the normal reference values in testing protocols. For example, normal reference values for the Mayo Clinic's SALCT test that determines cortisol level in saliva is <100 ng/dL; a saliva cortisol level higher than 100 ng/dL is thus an indication of hypercortisolemia. After being diagnosed with hypercortisolemia, the patient is subject to additional tests to confirm the presence of Cushing's syndrome.

c Cushing's Syndrome

At least one, preferably two or more, of the following tests are performed to diagnose Cushing's syndrome: 1) dexamethasone suppression test, which documents a loss of feedback inhibition of cortisol on the hypothalamic-pituitary-adrenal (HPA) axis; 2) 24-hour Urine Free Cortisol test, which assesses cortisol secretion in a 24-hour period; and 3) midnight salivary cortisol, which evaluates the loss of normal diurnal variation in cortisol secretion. If two of the three tests show abnormal cortisol levels, the Cushing's syndrome is confirmed.

The dexamethasone suppression test is typically used as a screen test for Cushing's syndrome. Dexamethasone is an exogenous steroid that binds glucocorticoid receptors in the anterior pituitary gland. When healthy individuals are treated with a low dose (1-2 mg) of dexamethasone, binding of dexamethasone to the glucocorticoid receptors provides negative feedback to the pituitary gland and results in suppression of ACTH secretion. The suppression of ACTH secretion, in turn, results in suppression of cortisol release and therefore a detectable decrease in cortisol level in circulation. In contrast, when patients having Cushing's syndrome are treated with a low dose of dexamethasone, no or little decrease in cortisol levels can be detected because of the excessive cortisol production associated with the disease. In one approach, the dexamethasone suppression test is performed by administering a low dose of dexamethasone, e.g., 1 mg, the night before at, e.g., 11 pm. The next morning, e.g., between 8-9 am; the patient's blood is then sampled and serum cortisol levels measured. Since normal subjects typically have serum cortisol levels reduced to less than 1.8 mg/dl, a serum cortisol level of more than 1.8 mg/dL is indicative of the presence of Cushing's syndrome.

The 24-hour Urine Free Cortisol test is the gold standard for diagnosing Cushing's syndrome. This test uses the principle that cortisol production is increased with Cushing's syndrome, and measurements of urinary excretion provide an integral estimate of that increase. A result more than the normal reference values is indicative of the presence of Cushing's syndrome. A 3 to 4-fold increase over normal reference values provides definite diagnosis of Cushing's syndrome; if this increase is present, no additional testing is required to confirm the diagnosis. For less dramatic increases in the urinary free-cortisol (UFC) level, other tests, such as the overnight dexamethasone suppression test and the midnight salivary cortisol test, as described above, are required.

The midnight saliva test is another test commonly used to confirm Cushing's syndrome. See the description of the test in the section above.

If the patient is confirmed to have Cushing's syndrome by two of the three tests, or by the detection of a 3 to 4-fold cortisol level increase in the 24-hour Urine Free Cortisol test, the next step is to measure ACTH to confirm he or she has ACTH-dependent Cushing's syndrome.

d ACTH-Dependent Cushing's Syndrome

There are two kinds of endogenous Cushing's syndrome: ACTH-dependent and ACTH-independent. The high cortisol level associated with ACTH-dependent Cushing's syndrome is caused by the overproduction of ACTH from a tumor, e.g., a pituitary tumor or an extrapituitary tumor. The excess cortisol level associated with ACTH-independent Cushing's syndrome, on the other hand, is caused by the overproduction of cortisol by a tumor in the adrenal gland or the overgrowth of the adrenal gland—either of which inhibits ACTH production and release. Thus, the ACTH levels are high in patients having ACTH-dependent Cushing's syndrome but low or even undetectable in patients having ACTH-independent Cushing's syndrome.

The biological samples that are suitable for ACTH determination can be serum, plasma, saliva, urine, or any other biological fluid taken from a subject. The sample can be the same or different from the sample used for cortisol level measurement. In some cases, the same sample that is used to measure cortisol level can be used to measure ACTH level. In other cases, different samples are used to measure cortisol and ACTH levels. For example, the cortisol levels can be measured in saliva and the ACTH levels can be measured in plasma. In yet other cases, different samples of the same type are used to measure the levels.

The level of ACTH can be measured using various methods, including but not limited to, immunoassays, e.g., competitive immunoassay, radioimmunoassay, immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). Commercial kits for measuring ACTH are readily available, e.g., from Mayo clinic (Test ID: ACTH), Siemans Healthcare Global (Immulite® 2000 ACTH assay), and Roche Molecular Diagnostics (Catalog No. 03255751190).

A plasma ACTH concentration higher than the normal reference value indicates that the patient has ACTH-dependent Cushing's syndrome. Normal reference values vary depending on the assay method, type of sample, and timing of sample collection; like cortisol, ACTH in healthy individuals varies during a 24-hour period, reaching its highest level in the morning around 6-8 am and lowest at night around 11 pm. Various commercial kits provide the normal reference values in their testing protocols. For example, the normal reference values for Mayo Clinic Test ID: ACTH are about 10-60 pg/mL.

Patients diagnosed with ACTH-dependent Cushing's syndrome are selected, and the differential diagnosis performed as described below.

2. Method of Differential Diagnosis of ACTH-Dependent Cushing's Syndrome

The differential diagnosis method uses GRAs to discriminate between Cushing Disease and ectopic ACTH Cushing's syndrome, the two major forms of ACTH-dependent Cushing's syndrome. GRAs prevent cortisol from inhibiting both the CRH production in the hypothalamus and ACTH production in the pituitary gland through a negative feedback interaction, resulting in increased ACTH production and release. Patients with Cushing Disease have ACTH-producing tumors in the pituitary gland and thus will have a higher increase in ACTH level around the pituitary region than the periphery region (outside the pituitary region). In contrast, patients with ectopic ACTH syndrome have the tumor growing outside the pituitary gland and thus will have a higher ACTH increase in the periphery than around the pituitary region. Thus a pituitary-to-periphery ratio can be used to discriminate between the two major types of ACTH-dependent Cushing's syndrome.

a Administration of GRA

GRA is administered at a dosage that is sufficient to increase ACTH in the pituitary gland by at least two fold in persons with normal HPA functions. In one embodiment, the GRA is mifepristone. In one embodiment, mifepristone is administered orally to the patient. In one embodiment, the mifepristone is administered at 300-1500 mg. In one embodiment, the GRA is administered at 11 pm the night before IPSS.

b. IPSS

The pituitary ACTH is measured from the blood sample obtained from the left, right, or both inferior petrosal sinuses (IPSs), which drain the pituitary gland. The periphery ACTH level is determined from the blood sample from a periphery vein. The procedure of sampling from inferior petrosal sinuses (known as IPSS) and the periphery is typically performed by an interventional radiologist.

IPSS is typically performed in the morning after administration of GRA, e.g., between 8 and 10 am, by advancing one or two microcatheters from the femoral vein up to one or both inferior petrosal sinuses. Meanwhile, another microcatheter is advanced to a periphery vein, e.g., the jugular vein. Venogram, or a digital venography, which documents the position of the catheters, is used to ensure the proper placement of the catheter; sampling begins only after confirming the microcatheter is positioned well in the IPS. Two samplings are made, at 5-10 minutes apart, by drawing blood simultaneously from the IPSs and the jugular vein at each sampling. Samples obtained are immediately placed in EDTA-containing tubes on ice. In some cases, an IPSS is performed only on one sinus, i.e., the left or right sinus. In some cases, the IPSS is performed for both sinuses (BIPSS). BIPSS provides values of ACTH from both right and left sinuses, a comparison of which provides useful information as to which side of the pituitary gland the tumor is located.

c. Diagnosis Based on the Central-to-Peripheral ACTH Ratio with Reference to Prolactin The central-to-periphery ratio is the basis for the diagnosis; however the IPSS requires high level of expertise; since anomalous venous drainage, e.g., misplacement of the catheter tip when sampling the inferior petrosal sinus, may cause false negative results. In addition to IPSS venogram (described above), prolactin—which is also secreted by pituitary gland and circulated to the periphery—is often used as a marker for successful catheterization during IPSS. Prolactin levels are assessed from the same blood samples that are used for the ACTH analysis. A ratio of the central to periphery prolactin of more than 1.8 indicates successful catheterization.

Methods for measuring prolactin are known in the art. Useful assays include immunoassays, e.g., competitive immunoassay, radioimmunoassay, immunofluorometric enzyme assay, and ELISA; competitive protein-binding assay; and mass spectrometry, e.g., high-performance liquid chromatography/triple quadrupole-mass spectrometry (LC-MS/MS). Commercial kits for measuring prolactin are also readily available, e.g., from Abcam (Catalog #ab108655), R&D systems (Human Prolactin Quantikine ELISA Kit), and Cayman Chemical (Prolactin EIA Kit).

ACTH levels are determined using the methods described above. The patient's ACTH levels from one or both inferior petrosal sinuses are then compared with the ACTH levels in the periphery blood, and the petrosal sinus-to-periphery ACTH ratios are then determined. If the patient's inferior petrosal to periphery prolactin ratio is less than 1.8 (especially if less than 1.5)—an indication that the catheterization was improper—no diagnosis can be made and a new IPSS may need to be performed. If the patient's inferior petrosal-to-periphery prolactin ratio is more than 1.8 and the inferior petrosal-to-periphery ACTH ratio is greater than 3, he or she is then diagnosed as having Cushing Disease. If the patient's inferior petrosal-to-periphery prolactin ratio is more than 1.8 and the inferior petrosal-to periphery-ACTH ratio is less than 3, he or she is then diagnosed as having ectopic ACTH syndrome.

B. Establishing a Standard Control Level

As disclosed above, the differential diagnosis of ACTH dependent Cushing's syndrome involves comparisons of measurements of different hormones, e.g., prolactin, ACTH, and cortisol, with their respective normal reference values. In most cases, normal reference values, or standard control levels, are provided in the commercial kits that are used for the testing. Depending on circumstances, it may be necessary in some cases to establish a standard control level for the diagnosis. In order to establish a standard control for a particular sample type (e.g., a saliva sample, urine sample, plasma sample, or serum sample) for practicing the method of this disclosure, a group of healthy subjects, such as a group of subjects who do not have adrenal insufficiency, is selected. These individuals are within the appropriate parameters, if applicable, for the purpose of diagnosing adrenal insufficiency using the methods of the present invention. For instance, the individuals may be of similar age, gender, and comparable health status. Optionally, the individuals are of similar ethnic background.

The healthy status of the selected individuals can be confirmed by well-established, routinely employed methods, including but not limited to, general physical examination of the individuals and general review of their medical history.

Furthermore, the selected group of healthy individual must be of a reasonable size, such that the average amount, level, or concentration of cortisol, ACTH, or other steroid in the biological sample obtained from the group can be reasonably regarded as representative of the normal or average level among the general population of healthy individuals who do not experience adrenal insufficiency. Preferably, the selected group comprises at least 10 normal, healthy human subjects.

Once an average value of cortisol, ACTH, or other steroid is established on the individual values found in each subject of the selected healthy control group, this average, median, or representative value or profile is considered a standard control level. A standard deviation is also determined during the same process. In some cases, separate standard control levels may be established for separately defined groups having distinct characteristics such as age, sex or ethnic background.

C. Glucocorticoid Receptor Antagonists

The methods of the present invention generally provide administering a GRA. In some cases, the glucocorticoid receptor antagonist is a specific GRA. As used herein, a specific glucocorticoid receptor antagonist refers to a composition or compound which inhibits any biological response associated with the binding of a glucocorticoid receptor to an agonist by preferentially binding to the glucocorticoid receptor rather than to another nuclear receptor (NR). In some embodiments, the specific GRA binds preferentially to the glucocorticoid receptor rather than the mineralocorticoid receptor (MR), androgen receptor (AR), or progesterone receptor (PR). In an exemplary embodiment, the specific GRA binds preferentially to glucocorticoid receptor rather than the mineralocorticoid receptor (MR). In another exemplary embodiment, the specific GRA binds preferentially to the glucocorticoid receptor rather than the progesterone receptor (PR). In another exemplary embodiment, the specific GRA binds preferentially to the glucocorticoid receptor rather than the androgen receptor (AR). In yet another exemplary embodiment, the specific GRA binds preferentially to the glucocorticoid receptor in comparison to MR and PR, MR and AR, PR and AR, or MR, PR, and AR.

In a related embodiment, the specific GRA binds to the glucocorticoid receptor with an association constant ($K_d$) that is at least 10-fold less than the $K_d$ for other nuclear receptors. In another embodiment, the specific GRA binds to the glucocorticoid receptor with an association constant ($K_d$) that is at least 100-fold less than the $K_d$ for the other nuclear receptors. In another embodiment, the specific GRA binds to the glucocorticoid receptor with an association constant ($K_d$) that is at least 1000-fold less than the $K_d$ for the other nuclear receptors.

Generally, treatment can be provided by administering an effective amount of a GRA of any chemical structure or mechanism of action and a glucocorticosteroid of any chemical structure or mechanism of action. Provided herein, are classes of exemplary GRAs and specific members of such classes. However, one of skill in the art will readily recognize other related or unrelated GRAs that can be employed in the treatment methods described herein.

1. GRAs Having a Steroidal Backbone

In some embodiments, an effective amount of a GRA with a steroidal backbone is administered to a subject for treatment of an ACTH-secreting tumor. Steroidal GRAs can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create GRAs include modifications of the 11-β hydroxy group and modification of the 17-β side chain (See, e.g., Lefebvre, J. Steroid Biochem. 33:557-563, 1989).

Examples of steroidal GR antagonists include androgen-type steroidal compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and (17α)-17-hydroxy-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5:Supp. 1, S 148 (2002) disclose the compound (11β,17β)-11-(1,3-benzodioxol-5-yl)-17-hydroxy-17-(1-propynyl)estra-4,9-dien-3-one (ORG 34517), which in one embodiment, is administered in an amount effective to treat an ACTH-secreting tumor in a subject.

2. Removal or Substitution of the 11-β Hydroxy Group

Glucocorticoid antagonists with modified steroidal backbones comprising removal or substitution of the 11-β hydroxy group are administered in one embodiment of the invention. This class includes natural GRAs, including cortexolone, progesterone and testosterone derivatives, and synthetic compositions, such as mifepristone (Lefebvre, et al. supra). Preferred embodiments of the invention include all 11-β aryl steroid backbone derivatives because, in some cases, these compounds can be devoid of progesterone receptor (PR) binding activity (Agarwal, FEBS 217:221-226, 1987). In another embodiment an 11-β phenyl-aminodimethyl steroid backbone derivative, which is both an effective anti-glucocorticoid and anti-progesterone agent, is administered. These compositions can act as reversibly-binding steroid receptor antagonists. For example, when bound to a 11-β phenyl-aminodimethyl steroid, the steroid receptor can be maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-β-hydrox-11-β-(4-dimethyl-aminophenyl)17-α-(1-propynyl)estra-4,9-dien-3-one). Mifepristone has been shown to be a powerful antagonist of both the progesterone and glucocorticoid (GR) receptors. Thus, in some embodiments, the GRA administered to treat an ACTH-secreting tumor is mifepristone, or a salt, tautomer, or derivative thereof. In other embodiments, however, administration of mifepristone is specifically excluded as a GRA for treatment of an ACTH-secreting tumor.

Another 11-β phenyl-aminodimethyl steroid shown to have GR antagonist effects includes the dimethyl aminoethoxyphenyl derivative RU009 (RU39.009), 11-β-(4-dimethyl-aminoethoxyphenyl)-17-α-(propynyl-17-β-hydroxy-4,9-estradien-3-one) (see Bocquel, J. Steroid Biochem. Molec. Biol. 45:205-215, 1993). Another GR antagonist related to RU486 is RU044 (RU43.044) 17-β-hydrox-17-α-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions that are irreversible anti-glucocorticoids. Such compounds include α-ketomethanesulfonate derivatives of cortisol, including cortisol-21-mesylate (4-pregnene-11-β, 17-α, 21-triol-3, 20-dione-21-methane-sulfonate and dexamethasone-21-mesylate (16-methyl-9-α-fluoro-1,4-pregnadiene-11β, 17-α, 21-triol-3, 20-dione-21-methane-sulfonte). See Simons, J. Steroid Biochem. 24:25-32, 1986; Mercier, J. Steroid Biochem. 25:11-20, 1986; U.S. Pat. No. 4,296,206.

3. Modification of the 17-beta Side Chain Group

Steroidal anti-glucocorticoids which can be obtained by various structural modifications of the 17-β side chain are also used in the methods of the invention. This class includes synthetic antiglucocorticoids, such as dexamethasone-oxetanone, various 17, 21-acetonide derivatives and 17-beta-carboxamide derivatives of dexamethasone (Lefebvre, 1989, supra; Rousseau, Nature 279:158-160, 1979).

4. Other Steroid Backbone Modifications

GRAs used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-β side chain substituent, and particularly the size of that substituent, can play a key role in determining the extent of a steroid's antiglucocorticoid activity. Substitutions in the A ring of the steroid backbone can also be important. For example, 17-hydroxypropenyl side chains can, in some cases, decrease antiglucocorticoid activity in comparison to 17-propynyl side chain containing compounds.

Additional glucocorticoid receptor antagonists known in the art and suitable for practice of the invention include 21-hydroxy-6,19-oxidoprogesterone (See Vicent, Mol. Pharm. 52:749-753, 1997), Org31710 (See Mizutani, J Steroid Biochem Mol Biol 42(7):695-704, 1992), RU43044, RU40555 (See Kim, J Steroid Biochem Mol Biol. 67(3): 213-22, 1998), and RU28362.

5. Non-Steroidal Anti-Glucocorticoids as Antagonists

Non-steroidal glucocorticoid receptor antagonists (GRAs) are also used in the methods of the invention to treat adrenal insufficiency in a subject. These include synthetic mimetics and analogs of proteins, including partially peptidic, pseudopeptidic and non-peptidic molecular entities. For example, oligomeric peptidomimetics useful in the invention include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic & Medicinal Chem. 4:667-672, 1996).

Examples of non-steroidal GR antagonists include the GR antagonist compounds disclosed in U.S. Pat. Nos. 5,696,127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4α,9,10,10α(R)-octahydro-phenanthrene-2,7-diol ("CP 394531") and 4α(S)-benzyl-2(R)-prop-1-ynyl-1,2,3,4,4α,9,10,10α(R)-octahydrophenanthrene-2,7-diol ("CP 409069"); and the compounds disclosed in PCT International Application No. WO 96/19458, which describes non-steroidal compounds that are high-affinity, highly selective antagonists for steroid receptors, such as 6-substituted-1,2-dihydro-N-protected-quinolines.

In some embodiments, adrenal insufficiency is treated with an effective amount of a non-steroidal GRA having a cyclohexyl-pyrimidine backbone, a fused azadecalin backbone, a heteroaryl ketone fused azadecalin backbone, or an octahydro fused azadecalin backbone. For example, adrenal insufficiency can be treated with effective amounts of one of the foregoing GRAs and a GC or a GC analog. Exemplary GRAs having a cyclohexyl-pyrimidine backbone include those described in U.S. Pat. No. 8,685,973. In some cases, the GRA having a cyclohexyl-pyrimidine backbone has the following structure:

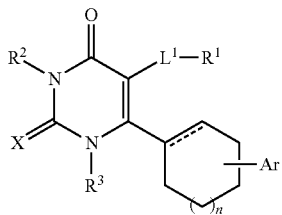

wherein
the dashed line is absent or a bond;
X is selected from the group consisting of O and S;
$R^1$ is selected from the group consisting of cycloalkyl, heterocycloalkyl, aryl and heteroaryl, optionally substituted with from 1 to 3 $R^{1a}$ groups;
each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloaloxy, $-OR^{1b}$, $-NR^{1b}R^{1c}$, $-C(O)R^{1b}$, $-C(O)OR^{1b}$, $-OC(O)R^{1b}$, $-C(O)NR^{1b}R^{1c}$, $-NR^{1b}C(O)R^{1c}$, $-SO_2R^{1b}$, $-SO_2NR^{1b}R^{1c}$, cycloalkyl, heterocycloalkyl, aryl and heteroaryl;
$R^{1b}$ and $R^{1c}$ are each independently selected from the group consisting of H and $C_{1-6}$ alkyl;
$R^2$ is selected from the group consisting of H, $C_{1-6}$ alkyl, $C_{1-6}$ alkyl-$OR^{1b}$, $C_{1-6}$ alkyl-$NR^{1b}R^{1c}$ and $C_{1-6}$ alkylene-heterocycloalkyl;
$R^3$ is selected from the group consisting of H and $C_{1-6}$ alkyl;
Ar is aryl, optionally substituted with 1-4 $R^4$ groups;
each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;
$L^1$ is a bond or $C_{1-6}$ alkylene; and
subscript n is an integer from 0 to 3,
or a salts and isomers thereof.

Exemplary GRAs having a fused azadecalin backbone include those described in U.S. Pat. Nos. 7,928,237; and 8,461,172. In some cases, the GRA having a fused azadecalin backbone has the following structure:

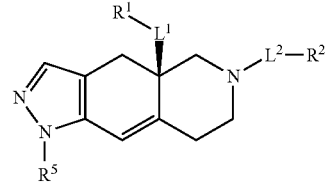

wherein
$L^1$ and $L^2$ are members independently selected from a bond and unsubstituted alkylene;
$R^1$ is a member selected from unsubstituted alkyl, unsubstituted heteroalkyl, unsubstituted heterocycloalkyl, $-OR^{1A}$, $-NR^{1C}R^{1D}$, $-C(O)NR^{1C}R^{1D}$, and $-C(O)OR^{1A}$, wherein
$R^{1A}$ is a member selected from hydrogen, unsubstituted alkyl and unsubstituted heteroalkyl,
$R^{1C}$ and $R^{1D}$ are members independently selected from unsubstituted alkyl and unsubstituted heteroalkyl,
wherein $R^{1C}$ and $R^{1D}$ are optionally joined to form an unsubstituted ring with the nitrogen to which they are attached, wherein said ring optionally comprises an additional ring nitrogen;
$R^2$ has the formula:

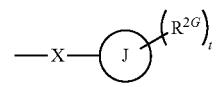

wherein
$R^{2G}$ is a member selected from hydrogen, halogen, unsubstituted alkyl, unsubstituted heteroalkyl, unsubstituted cycloalkyl, unsubstituted heterocycloalkyl, $-CN$, and $-CF_3$;
J is phenyl;
t is an integer from 0 to 5;
X is $-S(O_2)-$; and
$R^5$ is phenyl optionally substituted with 1-5 $R^{5A}$ groups, wherein
$R^{5A}$ is a member selected from hydrogen, halogen, $-OR^{5A1}$, $-S(O_2)NR^{5A2}R^{5A3}$, $-CN$, and unsubstituted alkyl, wherein
$R^{5A1}$ is a member selected from hydrogen and unsubstituted alkyl, and
$R^{5A2}$ and $R^{5A3}$ are members independently selected from hydrogen and unsubstituted alkyl,
or salts and isomers thereof.

Exemplary GRAs having a heteroaryl ketone fused azadecalin backbone include those described in U.S. 2014/0038926. In some cases, the GRA having a heteroaryl ketone fused azadecalin backbone has the following structure:

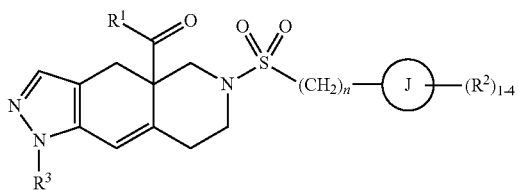

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;
- alternatively, two $R^2$ groups linked to the same carbon are combined to form an oxo group (=O);
- alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;
- $R^{2a}$ and $R^{2b}$ are each independently selected from the group consisting of hydrogen and $C_{1-6}$ alkyl;
- each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;
- each $R^{2d}$ is independently selected from the group consisting of hydrogen and $C_{1-6}$ alkyl, or two $R^{2d}$ groups attached to the same ring atom are combined to form (=O);
- $R^3$ is selected from the group consisting of phenyl and pyridyl, each optionally substituted with 1-4 $R^{3a}$ groups;
- each $R^{3a}$ is independently selected from the group consisting of hydrogen, halogen, and $C_{1-6}$ haloalkyl; and
- subscript n is an integer from 0 to 3;
or salts and isomers thereof.

Exemplary GRAs having an octohydro fused azadecalin backbone include those described in U.S. Provisional Patent Appl. No. 61/908,333, entitled Octahydro Fused Azadecalin Glucocorticoid Receptor Modulators, filed on Nov. 25, 2013. In some cases, the GRA having an octohydro fused azadecalin backbone has the following structure:

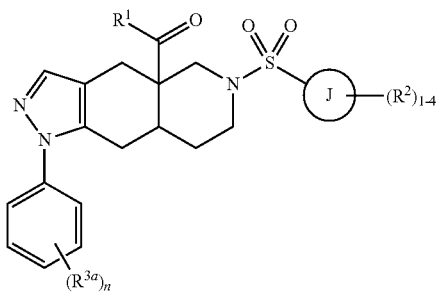

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;
- ring J is selected from the group consisting of an aryl ring and a heteroaryl ring having from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl having from 1 to 3 heteroatoms each independently selected from the group consisting of N, O and S;
- alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;
- $R^{2a}$, $R^{2b}$ and $R^{2c}$ are each independently selected from the group consisting of hydrogen and $C_{1-6}$ alkyl;
- each $R^{3a}$ is independently halogen; and
- subscript n is an integer from 0 to 3;
or salts and isomers thereof.

D. Pharmaceutical Compositions of Glucocorticoid Receptor Antagonists

The GRA compositions of the present disclosure can be prepared in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The GRA compositions of the present invention can also be administered by injection, that is, intravenously, intramuscularly, intracutaneously, subcutaneously, intraduodenally, or intraperitoneally. Also, the GRA compositions described herein can be administered by inhalation, for example, intranasally. Additionally, the GRA compositions of the present invention can be administered transdermally. The GRA compositions of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention provides pharmaceutical compositions of a GRA including a pharmaceutically-acceptable carrier or excipient and a GRA compound of the present invention.

For preparing pharmaceutical compositions from the GRA compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving one or more compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GRA compositions provided herein can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the GRA compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These GRA formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the GRA formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. *Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The GRA composition can also contain other compatible therapeutic agents. The compounds described herein can be used in combination with one another, with other active agents known to be useful in antagonizing a glucocorticoid receptor, or with adjunctive agents that may not be effective alone, but may contribute to the efficacy of the active agent.

E. Administration

The GRA compounds or compositions of the present invention can be delivered by any suitable means, including oral, parenteral (e.g., intravenous injection or intramuscular injection) and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

GRAs can be administered orally. For example, the GRA can be administered as a pill, a capsule, or liquid formulation as described herein. Alternatively, GRAs can be provided via parenteral administration. For example, the GRA can be administered intravenously (e.g., by injection or infusion). Additional methods of administration of the compounds described herein, and pharmaceutical compositions or formulations thereof, are described herein.

In some embodiments, the GRA is administered in one dose. In other embodiments, the GRA is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount will vary according to, for example, the GRA properties. To determine an effective dose, the GRA must elevate the level of ACTH by at least two fold in persons with normal Hypothalmus Pituitary Adrenal (HPA) function.

In some embodiments, the subject diagnosed as having adrenal insufficiency is administered a therapeutically effective amount of a GRA to ameliorate at least one symptom of adrenal insufficiency. In some case, therapeutically effective amount of the GRA can be administered to treat adrenal insufficiency, e.g., primary adrenal insufficiency or secondary adrenal insufficiency.

IV. Examples

Example 1 Diagnosis of Hypercortisolemia

A 45-year-old female visits her endocrinologist. She appears to have abdominal obesity, thin arms and legs, a round red face, and a fat lump between the shoulders. She has acne and reddish purple stretch marks in the body that are more than 1 cm wide. She describes having fragile skin that heals poorly, irregular menstruation, and she often feels changes in mood, headaches, and a chronic feeling of tiredness. Her physical examination records show that she has proximal muscle weakness and osteoporosis. Her blood tests indicate that she has low potassium, diabetes and elevated blood pressure. She has not been taken exogenous glucocorticoid drugs prior to this visit. Her endocrinologist suspects she has hypercortisolemia, and orders a late night saliva cortisol test for her.

She complies to the requirement not to brush, eat, or drink for 30 minutes prior to the saliva collection. At midnight she collected her saliva by placing a swab into her mouth, while rolling the swab, for approximately 2 minutes. The sample is assayed using Mayo Clinic Test ID: SALCT following the protocol provided with the test. The result shows that her cortisol level is 200 ng/dL, indicating that she has hypercortisolemia.

Example 2. Diagnosis of Cushing's Syndrome

After diagnosis of hypercortisolemia, additional tests are ordered for her to determine whether she has Cushing's syndrome. First, a dexamethasone suppression test is performed. She is given 1 mg of dexamethasone at 11 pm, and the next morning her blood sample are collected between 8-9 am. Serum are collected from the blood and measured for cortisol using Mayo Clinic Test ID: CORT (http://www.mayomedicallaboratories.com/test-catalog/Clinical+and+Interpretive/8545), according to manufacturer's instructions. Her serum cortisol level is 2.2 mcg/dl, consistent with the presence of Cushing's syndrome.

Next, a 24 hour urine collection is ordered to measure her urine free cortisol. 3 mL of her 24-hour urine specimen is collected into a container, with the addition of 10 gram of boric acid as a preservative. The sample is centrifuged and removed of precipitate before the assay. Cortisol content is analyzed using Mayo Clinic Test ID: COCOU, according to manufacturer's instructions (http://www.mayomedicallaboratories.com/test-catalog/Specimen/82948). The test shows a cortisol level of 180 mcg—4 fold of the upper limit of the normal range of cortisol for the test: 3.5-45 mcg. Based on her 24-hour urine excretion test result as well as her clinical symptoms, she is diagnosed as having Cushing's syndrome. The next step is to measure ACTH to differentiate between ACTH-dependent and ACTH-independent Cushing's syndrome.

Example 3. Diagnosis of ACTH-Dependent Cushing's Syndrome

A blood test is then performed to determine her plasma ACTH level. 1 mL of whole blood sample is drawn from her in the morning. The blood is spun down in a refrigerated centrifuge and the plasma is immediately separated from cells. 0.5 mL of the plasma sample is assayed for ACTH using Mayo Clinic Test ID: ACTH, following the manufacturer's instructions (http://www.mayomedicallaboratories.com/test-catalog/Specimen/8411). The result shows her plasma ACTH is 80 pg/mL, which indicates that she has ACTH-dependent Cushing's syndrome.

Example 4. Diagnosis of Cushing Disease

Following the diagnosis of ACTH dependent Cushing's syndrome, she then undergoes IPSS to identify the source of abnormal ACTH secretion, i.e., whether it is pituitary or ectopic. Mifepristone administration and IPSS are performed to determine the cause of her ACTH-dependent Cushing's syndrome. She first takes an oral dose of 300-1500 mg of mifepristone at 11 pm the night before IPSS. Mifepristone at this dose is sufficient to increase ACTH from the pituitary gland by at least two-fold in persons having normal hypothalamic-pituitary-adrenal axis (HPA) function. Between 8 to 10 am, an interventional radiologist performs a femoral microcatheterization, in which two 0.018 inch microcatheters are advanced from the femoral vein up to her right and left inferior petrosal sinuses (IPS). Another 0.018 microcatherter is inserted into the peripheral jugular vein. A 5,000 unit bolus of heparin is administered to the veins to prevent venous sinus thrombosis.

After the microcathers enter the sinuses and the jugular bulb, a diagnostic venography is performed, in which a rapid injection of contrast is performed to attempt to reflux contrast into the inferior petrosal sinus to guide placement of a microcatheter. After confirming the position of the microcatheter and positioning it well in the IPS, two samplings are made at 5-10 minutes apart. Blood samples are drawn simultaneously from the IPS and the jugular vein at each sampling and immediately placed in EDTA-containing tubes on ice.

One half of each blood sample is centrifuged for 10 minutes at 1,000-2,000 g to remove the cells and collect plasma. The other half is left undisturbed at room temperature for 30 minutes to clot, and serum is obtained after removal of the clot by a centrifugation. The plasma samples from both the jugular vein and the IPS are assayed for ACTH using Mayo Clinic's Test ID: ACTH, as described above. The serum samples are assayed for prolactin using Mayo Clinic's Test ID: PLPMA, following the manufacturer's instructions. The results show that the prolactin level in her left IPS is 25 ng/ml and right IPS is 24 ng/ml. The prolactin level in her jugular vein is 12 ng/ml. The ACTH level in her IPS is 800 pg/ml and the ACTH in her jugular vein is 200 pg/ml.

Her IPSs (both left and right) to jugular vein prolactin ratio is greater than 1.8, which reflects the correct central-to-periphery gradient, thus confirming the correct positioning of the catheterization. Her IPSs to jugular vein ACTH ratio is greater than 3, which indicates she has Cushing Disease.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of concurrently treating Cushing's syndrome and obtaining a measurement indicative of differential diagnosis of adrenocorticotropic hormone (ACTH)-dependent Cushing's syndrome in a patient where the differential diagnosis is between ectopic ACTH syndrome and Cushing's disease, the method comprising the steps of:
   administering a dose of mifepristone to a patient with Cushing's syndrome, hypercortisolemia, and an elevated ACTH level, wherein the amount of mifepristone administered to said patient is at least 300 milligrams (mg) and is no greater than 1500 mg; then,
   determining the ACTH concentration ratio from venous samples obtained from the patient at least two hours following said mifepristone administration, wherein said venous samples are obtained from a) the left or right inferior petrosal venous sinus and from b) a peripheral vein; and
   wherein an ACTH concentration ratio of greater than 3 for the ACTH concentration from an inferior petrosal venous sinus sample over the peripheral venous sample is diagnostic of Cushing's disease.

2. The method of claim 1, wherein said mifepristone is administered orally.

3. The method of claim 1, wherein the amount of mifepristone is 300 mg.

4. The method of claim 1, wherein the amount of mifepristone is greater than 300 mg and is less than 1500 mg.

5. The method of claim 1, wherein the amount of mifepristone is 1500 mg.

6. The method of claim 1, wherein a first and second sampling of the ACTH concentrations are taken 5-10 minutes apart from both the inferior petrosal venous sinus and a periphery venous sample.

7. The method of claim 1, comprising obtaining said venous samples, wherein said mifepristone is administered at about 11 PM the night preceding said obtaining the venous samples.

8. The method of claim 1, wherein the periphery venous sample is a jugular venous sample.

9. The method of claim 1, wherein said administering a dose of mifepristone comprises administering a plurality of daily doses of mifepristone for a period of not less than 5 weeks.

10. The method of claim 1 wherein the periphery venous sample is a jugular venous sample.

11. A method of concurrently treating Cushing's syndrome and obtaining a measurement indicative of differential diagnosis of adrenocorticotropic hormone (ACTH)-dependent Cushing's syndrome in a patient where the differential diagnosis is between ectopic ACTH syndrome and Cushing's disease, the method comprising the steps of:

Selecting a patient having Cushing's syndrome, said patient having hypercortisolemia and an elevated ACTH level;

determining the ACTH concentration ratio from said patient, where the patient has been administered a dose of mifepristone at least two hours prior to the removal of venous samples, wherein said mifepristone dose is at least 300 milligrams (mg) mifepristone and is no greater than 1500 mg mifepristone;

wherein the ACTH concentration ratio is derived from the ACTH concentrations in fluid obtained from either the left or right inferior petrosal venous sinus of the patient and from fluid obtained from a periphery venous sample obtained from the patient; and wherein an ACTH concentration ratio of greater than 3 for the ACTH concentration from the inferior venous sinus sample over the periphery venous sinus sample is indicative of Cushing's disease.

12. The method of claim 11, wherein said mifepristone is administered orally.

13. The method of claim 11, wherein the amount of mifepristone is 300 mg.

14. The method of claim 11, wherein the amount of mifepristone is greater than 300 mg and is less than 1500 mg.

15. The method of claim 11, wherein the amount of mifepristone is 1500 mg.

16. The method of claim 11, wherein a first and second sampling of the ACTH concentrations are taken 5-10 minutes apart from both the inferior petrosal venous sinus and a periphery venous sample.

17. The method of claim 11, comprising obtaining said venous samples, wherein said mifepristone is administered at about 11 PM the night preceding said obtaining the venous samples.

18. The method of claim 11, wherein the periphery venous sample is a jugular venous sample.

19. The method of claim 11, wherein said administering a dose of mifepristone comprises administering a plurality of daily doses of mifepristone for a period of not less than 5 weeks.

20. The method of claim 11 wherein the periphery venous sample is a jugular venous sample.

* * * * *